US00PP21925P2

(12) United States Plant Patent
Egger

(10) Patent No.: US PP21,925 P2
(45) Date of Patent: May 17, 2011

(54) ***TIARELLA* PLANT NAMED 'CASCADE CREEPER'**

(50) Latin Name: ***Tiarella* spp.**
Varietal Denomination: Cascade Creeper

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 12 days.

(21) Appl. No.: 12/653,643

(22) Filed: Dec. 14, 2009

(51) Int. Cl.
*A01H 5/00* (2006.01)

(52) U.S. Cl. ..... Plt./486

(58) Field of Classification Search ..... Plt./486
See application file for complete search history.

*Primary Examiner* — Wendy Haas
(74) *Attorney, Agent, or Firm* — Klarquist Sparkman, LLP

(57) ABSTRACT

A new and distinct cultivar of *Tiarella* plant characterized by large palmately-lobed leaves, with the terminal lobe the longest, a trailing habit, broad, dark brown markings following the veins, and excellent vigor.

1 Drawing Sheet

Botanical denomination: *Tiarella* spp.
Variety designation: 'Cascade Creeper'.
Cross Reference to sibling: *Tiarella* 'Happy Trails' (U.S. Plant patent application Ser. No. 12/653,642).

BACKGROUND OF THE INVENTION

The present invention relates to a new and distinct cultivar of a hardy herbaceous perennial of the genus *Tiarella*, and known by the cultivar name 'Cascade Creeper'. The genus *Tiarella* is a member of the family Saxifragaceae.

The new cultivar originated from a planned breeding program as a cross between *Tiarella* 27-04, a proprietary, unreleased trailing *Tiarella* as the seed parent and massed proprietary trailing *Tiarella* as the pollen parent. The exact pollen parent is unknown. Compared to the seed parent, *Tiarella* 27-04, the new cultivar is has a larger, more deeply cut leaf. Compared to other trailing *Tiarella* on the market the new cultivar has a more cut leaf and has a larger, darker central pattern on the leaf.

SUMMARY OF THE INVENTION

This plant is characterized by the following:

1. large palmately-lobed leaves, with the terminal lobe the longest,
2. a trailing habit,
3. broad, dark brown markings following the veins,
4. and excellent vigor.

The new variety has been reproduced only by asexual propagation (division and micropropagation). Each of the progeny exhibits identical characteristics to the original plant. Asexual propagation by division and micropropagation using standard techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a 9-month-old *Tiarella* 'Cascade Creeper' in bloom growing in 30 cm pots in a greenhouse in Canby, Oreg.

FIG. 2 shows a close up with the flower.

DETAILED PLANT DESCRIPTION

The following is a detailed description of the new *Tiarella* hybrid based on observations of six-month-old plants grown in 8.5 cm pots in a cool greenhouse in Canby, Oreg. Canby is Zone 8 on the USDA Hardiness map. Temperatures range from a high of 95 degrees F. in August to an average low of 32 degrees F. in January. Normal rainfall in Canby is 42.8 inches per year. The color descriptions are all based on The Royal Horticultural Society Colour Chart, 1999 edition.

Plant:

*Type.*—Herbaceous perennial.
*Hardiness.*—USDA Zones 4 to 9.
*Form.*—Clumping and trailing.
*Size.*—27 cm wide and 12 cm high from the soil to the top of the foliage.
*Vigor.*—Excellent.
*Roots.*—Fibrous, freely branching, fine, and white in color; roots develop easily from cuttings.

Stem: From basal clump.

*Size.*—12 cm long and 2.5 mm wide.
*Habit.*—Decumbent.
*Internode length.*—Grows to 4 cm.
*Color.*—Grey Brown 199D tinted Greyed Purple 186A.

Foliage:

*Type.*—Simple.
*Arrangement.*—Rosette and alternate.
*Shape.*—Ovate.
*Lobing.*—Variable, 5 to 7 main lobes, the terminal lobe is the longest, each main lobe with 0 to 2 lateral lobes.
*Margins.*—Entire to sometimes crenate on top half of a lobe.
*Venation.*—Palmate.
*Apex.*—Mucronulate.
*Base.*—Cordate, usually overlapping.
*Blade.*—Grows to 14 cm long and 10 cm wide.
*Surface.*—Hispid top and bottom.
*Petiole description.*—10 cm to 12 cm long and 2 mm wide, hirsute, between Greyed Purple 187A and Grey Brown 200A.

*Leaf color.*—Spring topside, Green 137A, with a dark pattern along the veins covering 50% of the leaf Black 202A; bottom side Yellow Green 147D where green on top and darker where black on top.

Inflorescence:

*Type.*—Raceme.

*Size.*—Grows to 19 cm long and 2.5 cm wide.

*Flower number.*—30 to 60 per raceme.

*Raceme number.*—5 main.

*Bloom period.*—April to May with sporadic rebloom throughout the summer and fall.

*Peduncle.*—Decumbent, branched and leafy (leaves variable and becoming smaller in size next to flowers, petiolate), grows to 43 cm long and 2.5 mm at the widest point, between Greyed Purple 186A and Grey Brown 200A.

*Pedicel.*—4 mm long, hispid, between Greyed Purple 186A and Greyed Purple 186C.

*Lastingness.*—A raceme blooms for about 3 weeks.

Flower bud:

*Size.*—3 mm deep and 2 mm wide.

*Description.*—Ovoid, down facing until open.

*Color.*—Purple 75B.

Flower:

*Type.*—Perfect, actinomorphic, sepals petaloid.

*Shape.*—Rotate.

*Flower size.*—7 mm wide and 5 mm deep including stamens and pistil.

*Corolla.*—5 petals, each 4 mm long and 1 mm wide, lanceolate with a clawed base, acuminate, entire, White 155D and glabrous on both sides.

*Calyx.*—5 sepals, petaloid, parted almost to the base, reflexed, Purple 75D inside and outside, lanceolate, acute, entire and sometime undulate, lobes 3 mm long and 1.5 mm wide.

*Stamens.*—10, conspicuously exerted; filaments 5 mm long, White 155D; anthers undehisced Orange 29A; pollen Orange 25C.

*Pistil.*—1, White 155A, 5 mm long.

*Fragrance.*—None.

Fruit: A one-celled capsule, beak-like, composed of two unequal parts; 0.7 cm long, Brown 200C.

Seeds: 1 mm long, minute, oval, Black 202A, fertile.

Pest and disease resistance: This new hybrid shows good mildew tolerance, the main problem for *Tiarella*. No major pest problems. It is susceptible to root weevils like all *Tiarella*.

I claim:

1. A new and distinct cultivar of *Tiarella* plant herein illustrated and described.

* * * * *

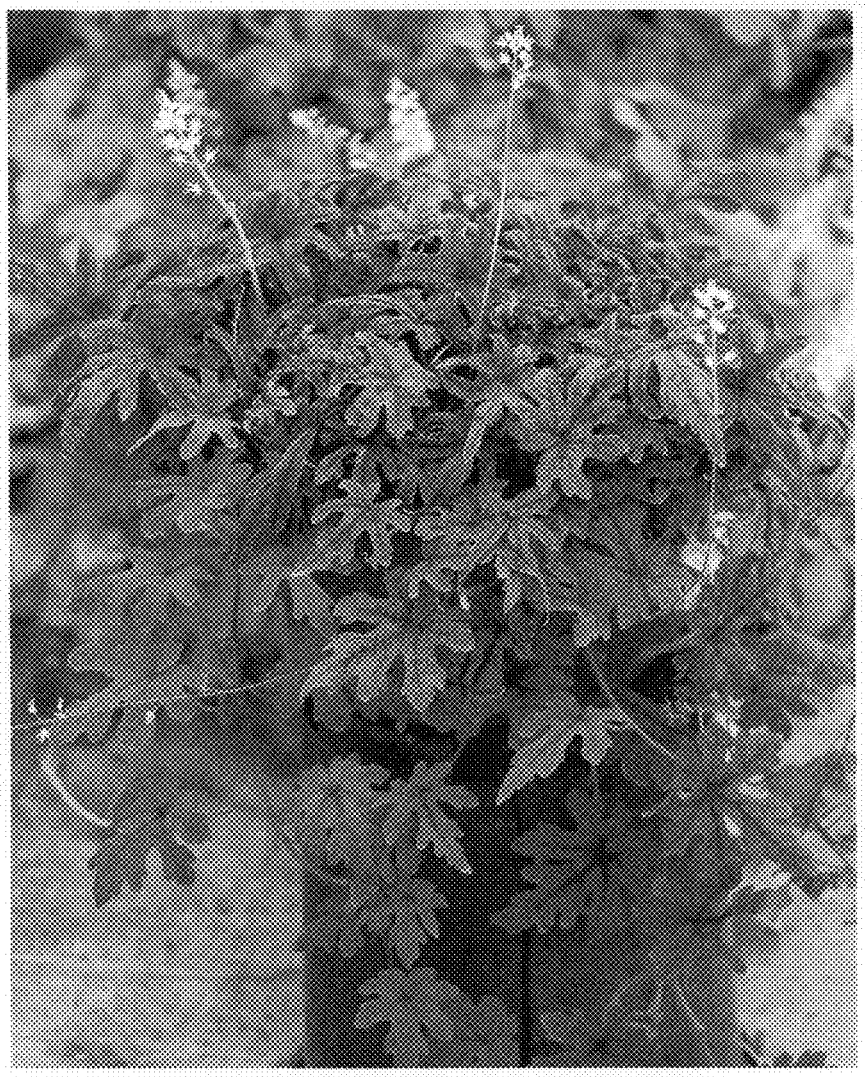
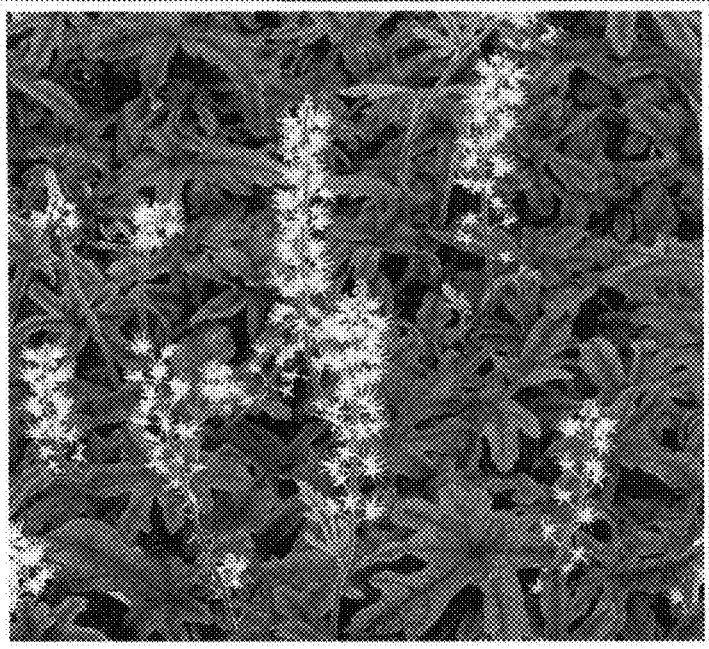
Figure 1 above,
Figure 2 below.